(12) United States Patent
Gronberg et al.

(10) Patent No.: US 9,870,628 B2
(45) Date of Patent: Jan. 16, 2018

(54) IMAGE RECONSTRUCTION BASED ON ENERGY-RESOLVED IMAGE DATA FROM A PHOTON-COUNTING MULTI-BIN DETECTOR

(71) Applicant: PRISMATIC SENSORS AB, Stockholm (SE)

(72) Inventors: Fredrik Gronberg, Stockholm (SE); Mats Persson, Vasterhaninge (SE); Hans Bornefalk, Vallentuna (SE)

(73) Assignee: Prismatic Sensors AB, Stockholm (SE)

( * ) Notice: Subject to any disclaimer, the term of this patent is extended or adjusted under 35 U.S.C. 154(b) by 0 days.

(21) Appl. No.: 15/505,296

(22) PCT Filed: Mar. 18, 2015

(86) PCT No.: PCT/SE2015/050316
§ 371 (c)(1),
(2) Date: Feb. 21, 2017

(87) PCT Pub. No.: WO2016/148616
PCT Pub. Date: Sep. 22, 2016

(65) Prior Publication Data
US 2017/0270692 A1 Sep. 21, 2017

(51) Int. Cl.
*G06K 9/00* (2006.01)
*G06T 11/00* (2006.01)
(Continued)

(52) U.S. Cl.
CPC ............ *G06T 11/003* (2013.01); *A61B 6/032* (2013.01); *A61B 6/4241* (2013.01); *A61B 6/463* (2013.01);
(Continued)

(58) Field of Classification Search
CPC ... G06T 11/003; G06T 2210/41; A61B 6/032; A61B 6/4241; A61B 6/463; A61B 6/5205; A61B 6/5241; G01N 23/046
See application file for complete search history.

(56) References Cited

U.S. PATENT DOCUMENTS 6,226,352 B1 * 5/2001 Salb ..................... A61B 6/4035
378/143
6,950,492 B2 * 9/2005 Besson .................. A61B 6/032
378/16
(Continued)

FOREIGN PATENT DOCUMENTS

WO 2007034359 A2 3/2007
WO 2015/156711 A1 10/2015

OTHER PUBLICATIONS

International Search Report, dated Nov. 30, 2015, from corresponding PCT application No. PCT/SE2015/050316.
(Continued)

*Primary Examiner* — Gregory M Desire
(74) *Attorney, Agent, or Firm* — Young & Thompson

(57) ABSTRACT

There is provided a method of image reconstruction based on energy-resolved image data from a photon-counting multi-bin detector or an intermediate storage. The method comprises processing (S1) the energy-resolved image data by performing at least two separate basis decompositions using different number of basis functions for modeling linear attenuation, wherein a first basis decomposition is performed using a first smaller set of basis functions to obtain at least one first basis image representation, and wherein a second basis decomposition is performed using a second larger set of basis functions to obtain at least one second basis image representation. The method also comprises reconstructing a first image based on said at least one first basis image representation obtained from the first basis (Continued)

decomposition, and combining the first image with information representative of said at least one second basis image representation.

4 Claims, 9 Drawing Sheets

(51) Int. Cl.
    *G01N 23/04* (2006.01)
    *A61B 6/03* (2006.01)
    *A61B 6/00* (2006.01)
(52) U.S. Cl.
    CPC .......... *A61B 6/5205* (2013.01); *A61B 6/5241* (2013.01); *G01N 23/046* (2013.01); *G06T 2210/41* (2013.01)

(56) References Cited

U.S. PATENT DOCUMENTS

| | | | |
|---|---|---|---|
| 7,272,429 B2* | 9/2007 | Walker | A61B 6/032 378/4 |
| 7,724,865 B2* | 5/2010 | Wu | A61B 6/032 378/4 |
| 7,756,239 B2 | 7/2010 | Wu et al. | |
| 7,873,201 B2 | 1/2011 | Eilbert et al. | |
| 8,306,180 B2* | 11/2012 | Zhang | G01V 5/005 378/4 |
| 8,311,181 B2* | 11/2012 | Thomsen | G06T 11/006 378/5 |
| 8,378,310 B2* | 2/2013 | Bornefalk | G06T 11/005 250/370.01 |
| 8,588,494 B2 | 11/2013 | De Man et al. | |
| 8,705,822 B2* | 4/2014 | Yu | G06T 11/006 378/5 |
| 8,855,385 B2 | 10/2014 | Kriston et al. | |
| 2004/0202360 A1* | 10/2004 | Besson | G06T 5/008 382/131 |
| 2007/0237288 A1* | 10/2007 | Tkaczyk | A61B 6/032 378/5 |
| 2009/0123048 A1 | 5/2009 | Leroux et al. | |
| 2009/0214095 A1 | 8/2009 | Wu et al. | |
| 2010/0027743 A1* | 2/2010 | Engel | G01T 1/1647 378/62 |
| 2010/0061504 A1 | 3/2010 | Proksa | |
| 2011/0150183 A1 | 6/2011 | Wu et al. | |
| 2011/0194668 A1* | 8/2011 | Kanno | A61B 6/032 378/4 |
| 2011/0268335 A1 | 11/2011 | Kunze et al. | |
| 2012/0063658 A1 | 3/2012 | Leroux et al. | |
| 2013/0108024 A1* | 5/2013 | Parsons | H01J 35/08 378/121 |
| 2014/0005971 A1* | 1/2014 | Roessl | G06T 11/005 702/104 |
| 2014/0369458 A1 | 12/2014 | Shen et al. | |
| 2014/0376687 A1* | 12/2014 | Alessio | A61B 6/504 378/5 |
| 2015/0178975 A1* | 6/2015 | Chatterjee | G06T 15/04 345/587 |

OTHER PUBLICATIONS

Mendonca, Paulo RS, Peter Lamb, and Dushyant V. Sahani. "A flexible method for multi-material decomposition of dual-energy CT images." IEEE transactions on medical imaging 33.1 (2014): 99-116.

Schirra, Carsten O., et al. "Statistical reconstruction of material decomposed data in spectral CT." IEEE transactions on medical imaging 32.7 (2013): 1249-1257.

Nuyts, Johan, et al. "Modelling the physics in the iterative reconstruction for transmission computed tomography." Physics in medicine and biology 58.12 (2013): R63-R96.

Szczykutowicz, Timothy P., and Guang-Hong Chen. "Dual energy CT using slow kVp switching acquisition and prior image constrained compressed sensing." Physics in medicine and biology 55.21 (2010): 6411-6429.

Alvarez, Robert E. "Dimensionality and noise in energy selective x-ray imaging." Medical physics, vol. 40, No. 11 (2013): 111909-1-13.

Alvarez, R.E., and A. Macovski. "Energy-selective reconstructions in x-ray computerized tomography." Physics in medicine and biology, vol. 21, No. 5 (1976): 733-744.

Bornefalk, Hans. "XCOM intrinsic dimensionality for low-Z elements at diagnostic energies." Medical physics, vol. 39, No. 2 (2012): 654-657.

Roessl, E., and C. Herrmann. "Cramér-Rao lower bound of basis image noise in multiple-energy x-ray imaging." Physics in medicine and biology, vol. 54, No. 5 (2009): 1307-1318.

Roessl, E., and R. Proksa. "K-edge imaging in x-ray computed tomography using multi-bin photon counting detectors." Physics in medicine and biology, vol. 52, No. 15 (2007): 4679-4696.

Tapiovaara, M.J., and R. Wagner. "SNR and DQE analysis of broad spectrum x-ray imaging." Physics in Medicine and Biology, vol. 30, No. 6 (1985): 519-529.

* cited by examiner

IMAGE RECONSTRUCTION BASED ON ENERGY-RESOLVED IMAGE DATA FROM A PHOTON-COUNTING MULTI-BIN DETECTOR

TECHNICAL FIELD

The proposed technology generally relates to x-ray imaging and corresponding imaging reconstruction and imaging tasks. In particular, the proposed technology relates to a method and system for image reconstruction, a corresponding imaging system and a corresponding computer program and computer-program product, as well as an arrangement for visualization and/or quantification of an in vivo compound or element not exhibiting k absorption edges.

BACKGROUND

Radiographic imaging such as x-ray imaging has been used for years in medical applications and for non-destructive testing.

Normally, an x-ray imaging system includes an x-ray source and an x-ray detector consisting of multiple detector elements. The x-ray source emits x-rays, which pass through a subject or object to be imaged and are then registered by the detector. Since some materials absorb a larger fraction of the x-rays than others, an image is formed of the interior of the subject or object.

An x-ray computed tomography (CT) system includes an x-ray source and an x-ray detector arranged in such a way that projection images of the subject or object can be acquired in different view angles covering at least 180 degrees. This is most commonly achieved by mounting the source and detector on a support that is able to rotate around the subject or object. An image containing the projections registered in the different detector elements for the different view angles is called a sinogram. In the following, a collection of projections registered in the different detector elements for different view angles will be referred to as a sinogram even if the detector is two-dimensional, making the sinogram a three-dimensional image.

A further development of x-ray imaging is energy-resolved x-ray imaging, also known as spectral x-ray imaging, where the x-ray transmission is measured for several different energy levels. This can be achieved by letting the source switch rapidly between two different emission spectra, by using two or more x-ray sources emitting different x-ray spectra, or by using an energy-discriminating detector which measures the incoming radiation in two or more energy levels. One example of such a detector is a multi-bin photon-counting detector, where each registered photon generates a current pulse which is compared to a set of thresholds, thereby counting the number of photons incident in each of a number of energy bins.

A spectral x-ray projection measurement results in one projection image for each energy level. A weighted sum of these can be made to optimize the contrast-to-noise ratio (CNR) for a specified imaging task as described in Tapiovaara and Wagner, "SNR and DQE analysis of broad spectrum X-ray imaging", Phys. Med. Biol. 30, 519.

Another technique enabled by energy-resolved x-ray imaging is basis material decomposition. This technique utilizes the fact that all substances built up from elements with low atomic number, such as human tissue, have linear attenuation coefficients $\mu(E)$ whose energy dependence can be expressed, to a good approximation, as a linear combination of two basis functions:

$$\mu(E) = a_1 f_1(E) + a_2 f_2(E).$$

where $f_i$ are the basis functions and $a_i$ are the corresponding basis coefficients. If there is one or more element in the imaged volume with high atomic number, high enough for a k-absorption edge to be present in the energy range used for the imaging, one basis function must be added for each such element. In the field of medical imaging, such k-edge elements can typically be iodine or gadolinium, substances that are used as contrast agents.

Basis material decomposition has been described in Alvarez and Macovski, "Energy-selective reconstructions in X-ray computerised tomography", Phys. Med. Biol. 21, 733. In basis material decomposition, the integral of each of the basis coefficients, $A_i = \int_l a_i dl$ for $i=1, \ldots, N$ where N is the number of basis functions, is inferred from the measured data in each projection ray from the source to a detector element. In one implementation, this is accomplished by first expressing the expected registered number of counts in each energy bin as a function of $A_i$:

$$\lambda_i = \int_{E=0}^{\infty} S_i(E) \exp\left(-\sum_{j=1}^{N} A_j f_j(E)\right) dE$$

Here, $\lambda_i$ is the expected number of counts in energy bin i, E is the energy, $S_i$ is a response function which depends on the spectrum shape incident on the imaged object, the quantum efficiency of the detector and the sensitivity of energy bin i to x-rays with energy E. Even though the term "energy bin" is most commonly used for photon-counting detectors, this formula can also describe other energy resolving x-ray systems such as multi-layer detectors or kVp switching sources.

Then, the maximum likelihood method may be used to estimate $A_i$, under the assumption that the number of counts in each bin is a Poisson distributed random variable. This is accomplished by minimizing the negative log-likelihood function, see Roessl and Proksa, K-edge imaging in x-ray computed tomography using multi-bin photon counting detectors, Phys. Med. Biol. 52 (2007), 4679-4696:

$$\hat{A}_1, \ldots, \hat{A}_N = \underset{A_1, \ldots, A_N}{\operatorname{argmin}} \sum_{i=1}^{M_b} \lambda_i(A_1, \ldots, A_N) - m_i \ln \lambda_i(A_1, \ldots, A_N)$$

where $m_i$ is the number of measured counts in energy bin i and $M_b$ is the number of energy bins.

When the resulting estimated basis coefficient line integral $\hat{A}_i$ for each projection line is arranged into an image matrix, the result is a material specific projection image, also called a basis image, for each basis i. This basis image can either be viewed directly (e.g. in projection x-ray imaging) or taken as input to a reconstruction algorithm to form maps of basis coefficients $a_i$ inside the object (e.g. in CT). Anyway, the result of a basis decomposition can be regarded as one or more basis image representations, such as the basis coefficient line integrals or the basis coefficients themselves.

However, a well-known limitation of this technique is that the variance of the estimated line integrals normally increases with the number of bases used in the basis decomposition. Among other things, this results in an unfortunate trade-off between improved tissue quantification and increased image noise.

SUMMARY

It is an object to provide an improved method of image reconstruction.

It is also an object to provide an improved system for image reconstruction.

It is another object to provide an imaging system.

Yet another object is to provide a corresponding computer program and computer-program product.

It is also an object to provide an arrangement for visualization and/or quantification of an in vivo compound or element not exhibiting k absorption edges.

These and other objects are met by embodiments of the proposed technology.

According to a first aspect, there is provided a method of image reconstruction based on energy-resolved image data from a photon-counting multi-bin detector or an intermediate storage. The method comprises:

processing the energy-resolved image data by performing at least two separate basis decompositions using different number of basis functions for modeling linear attenuation, wherein a first basis decomposition is performed using a first smaller set of basis functions to obtain at least one first basis image representation, and wherein a second basis decomposition is performed using a second larger set of basis functions to obtain at least one second basis image representation; and reconstructing a first image based on said at least one first basis image representation obtained from the first basis decomposition; and combining the first image with information representative of said at least one second basis image representation.

According to a second aspect, there is provided a system for image reconstruction based on energy-resolved image data from a photon-counting multi-bin detector or an intermediate storage. The system is configured to process the energy-resolved image data by performing at least two separate basis decompositions using different number of basis functions for modeling linear attenuation. The system is configured to perform a first basis decomposition using a first smaller set of basis functions to obtain at least one first basis image representation. The system is also configured to perform a second basis decomposition using a second larger set of basis functions to obtain at least one second basis image representation. The system is further configured to reconstruct a first image based on said at least one first basis image representation obtained from the first basis decomposition. The system is also configured to combine the first image with information representative of said at least one second basis image representation.

According to a third aspect, there is provided an imaging system comprising the system for image reconstruction according to the second aspect.

According to a fourth aspect, there is provided a computer program comprising instructions, which when executed by at least one processor, cause the at least one processor to:

process energy-resolved image data from a photon-counting multi-bin detector or an intermediate storage by performing at least two separate basis decompositions using different number of basis functions for modeling linear attenuation, wherein a first basis decomposition is performed using a first smaller set of basis functions to obtain at least one first basis image representation, and wherein a second basis decomposition is performed using a second larger set of basis functions to obtain at least one second basis image representation; and perform image reconstruction based on said at least one first basis image representation obtained from the first basis decomposition and said at least one second basis image representation obtained from the second basis decomposition.

According to a fifth aspect, there is provided a corresponding computer-program product comprising a computer-readable medium having stored thereon a computer program of the fourth aspect.

According to a sixth aspect, there is provided an arrangement for visualization and/or quantification of an in vivo compound or element not exhibiting k absorption edges, comprising:

a photon-counting multi-bin detector mountable in a computed tomography gantry, and a processing device capable of decomposing multi-bin projection measurements in at least two parallel processing paths using different number of basis functions for reconstructing corresponding images, a graphic device capable of merging images resulting from the parallel processing paths including at least one reconstructed display image and a reconstructed image, for example an overlay map, of said compound or element.

In this way, efficient high-quality image reconstruction and/or quantification can be achieved. By way of example, the apparent trade-off between improved tissue quantification and increased image noise can be overcome.

Other advantages will be appreciated when reading the detailed description.

BRIEF DESCRIPTION OF THE DRAWINGS

The embodiments, together with further objects and advantages thereof, may best be understood by making reference to the following description taken together with the accompanying drawings, in which.

DETAILED DESCRIPTION

Throughout the drawings, the same reference designations are used for similar or corresponding elements.

For a better understanding of the proposed technology it may be useful to start by briefly describing a non-limiting example of an imaging system.

Figure 1:
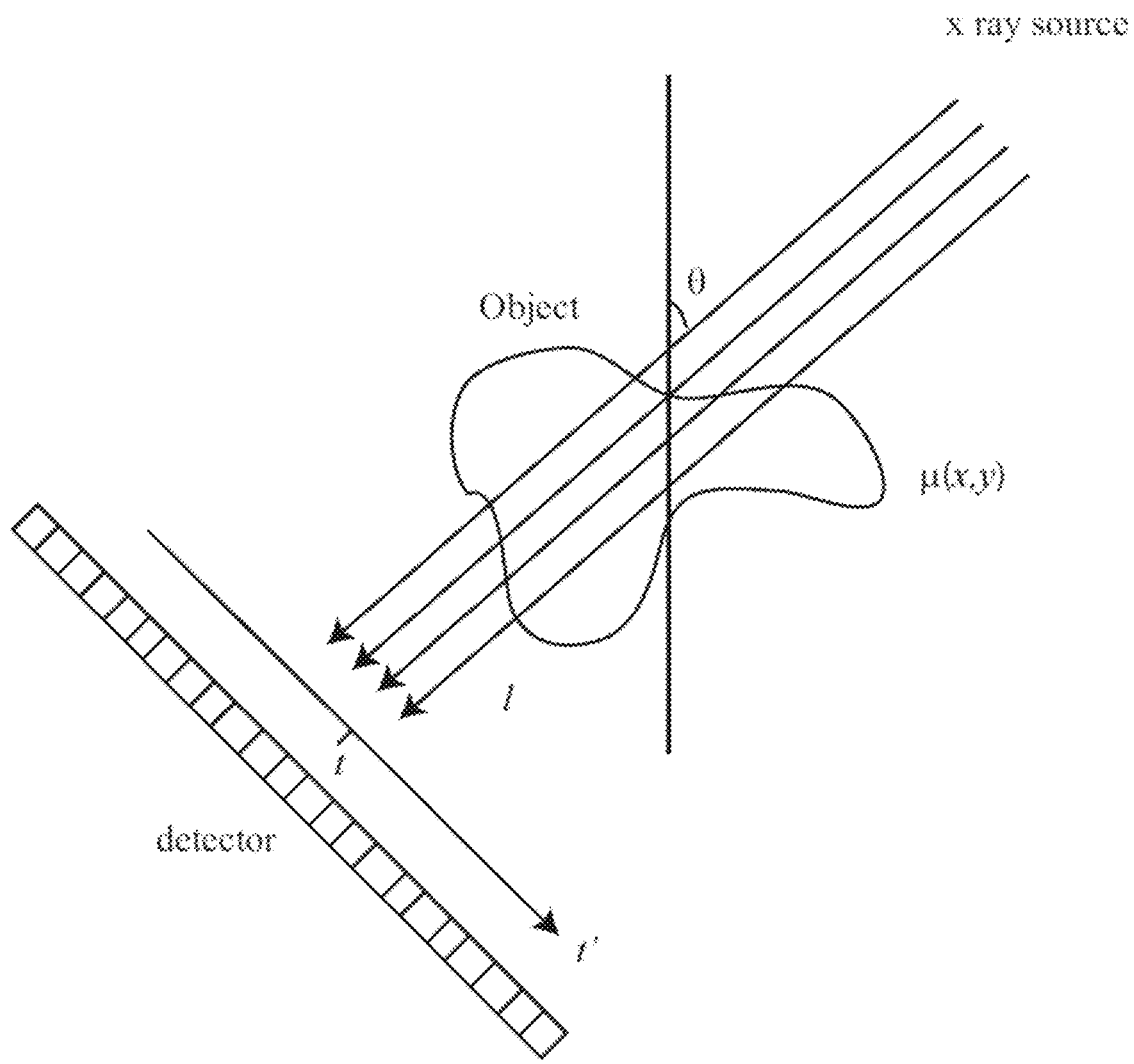
FIG. 1 is a schematic diagram illustrating an example of an imaging system setup showing projection lines from a source through an object to a detector.

FIG. 1 is a schematic diagram illustrating an example of an imaging system setup showing projection lines from a source through an object to a detector.

Figure 2:
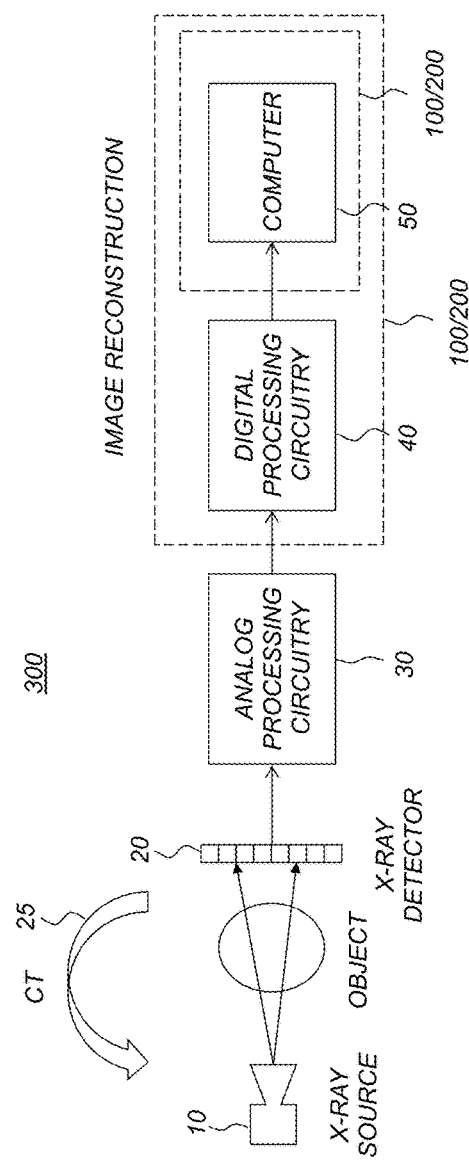
FIG. 2 is a schematic diagram illustrating an example of an x-ray imaging system and an image reconstruction subsystem.

As illustrated in the example of FIG. 2, an x-ray imaging system comprises an x-ray source 10, which emits x-rays; an x-ray detector 20, which detects the x-rays after they have passed through the object; analog processing circuitry 30, which processes the raw electrical signal from the detector and digitizes it; digital processing circuitry 40 which may carry out further processing operations on the measured data such as applying corrections, storing it temporarily, or filtering; and a digital computer 50 which stores the processed data and may perform further post-processing and/or image reconstruction. The overall detector may be regarded as the x-ray detector 20, or the x-ray detector 20 combined with the associated analog processing circuitry 30. The digital part including the digital processing circuitry 40 and/or the computer 50 may be regarded as an image reconstruction system 100/200, which performs image reconstruction based on the image data from the x-ray detector. The image reconstruction system 100/200 may thus be seen as the computer 50, or alternatively the combined system of the digital processing circuitry 40 and the computer 50, or possibly the digital processing circuitry 40 by itself if the digital processing circuitry is further specialized also for image reconstruction. The x-ray source 10 and/or the x-ray detector 20 may be arranged as part of a Computed Tomography (CT) system, e.g. mountable in a CT gantry.

Figure 3:
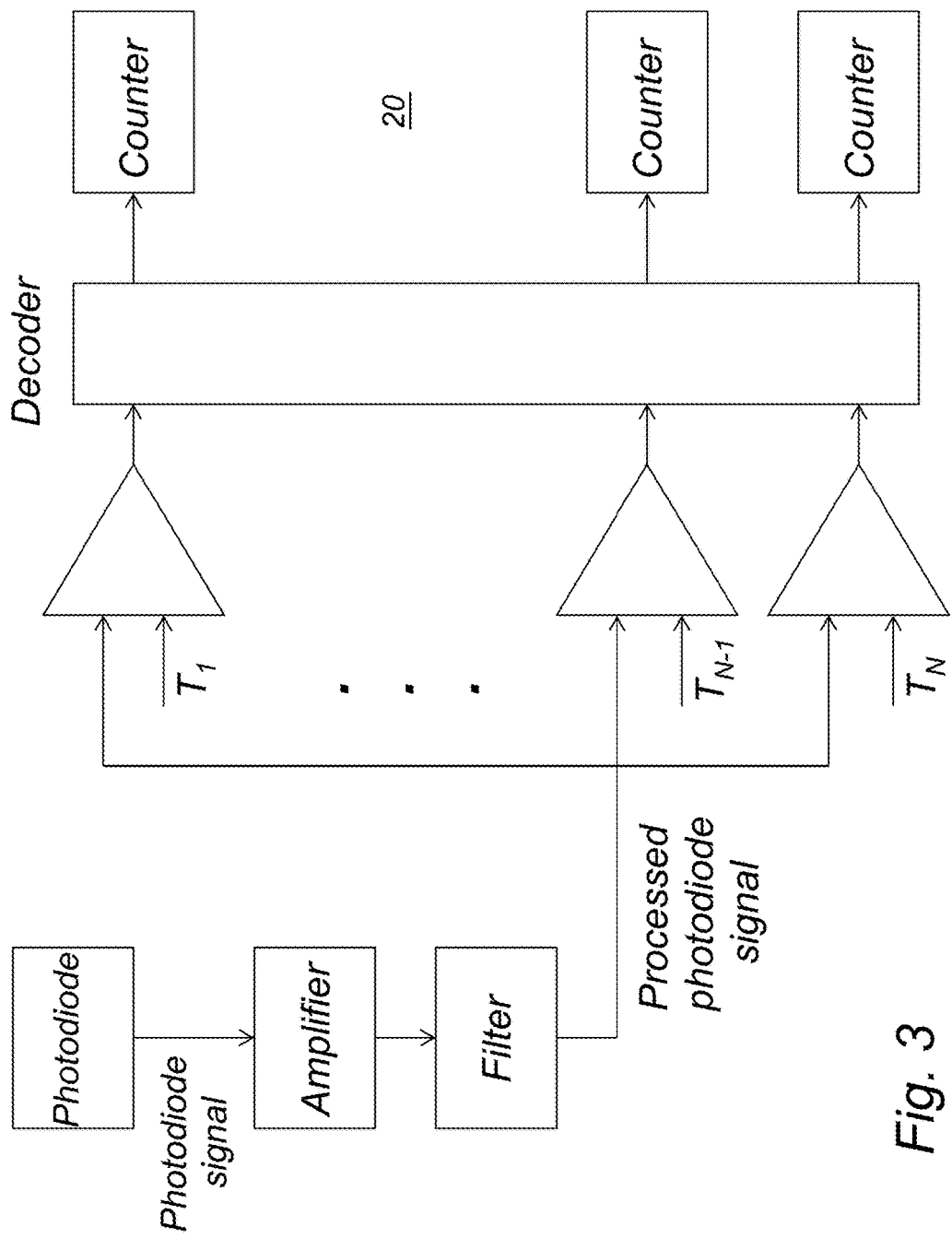
FIG. 3 is a schematic diagram illustrating an example of a photon-counting detector with several energy thresholds.
Figure 4:
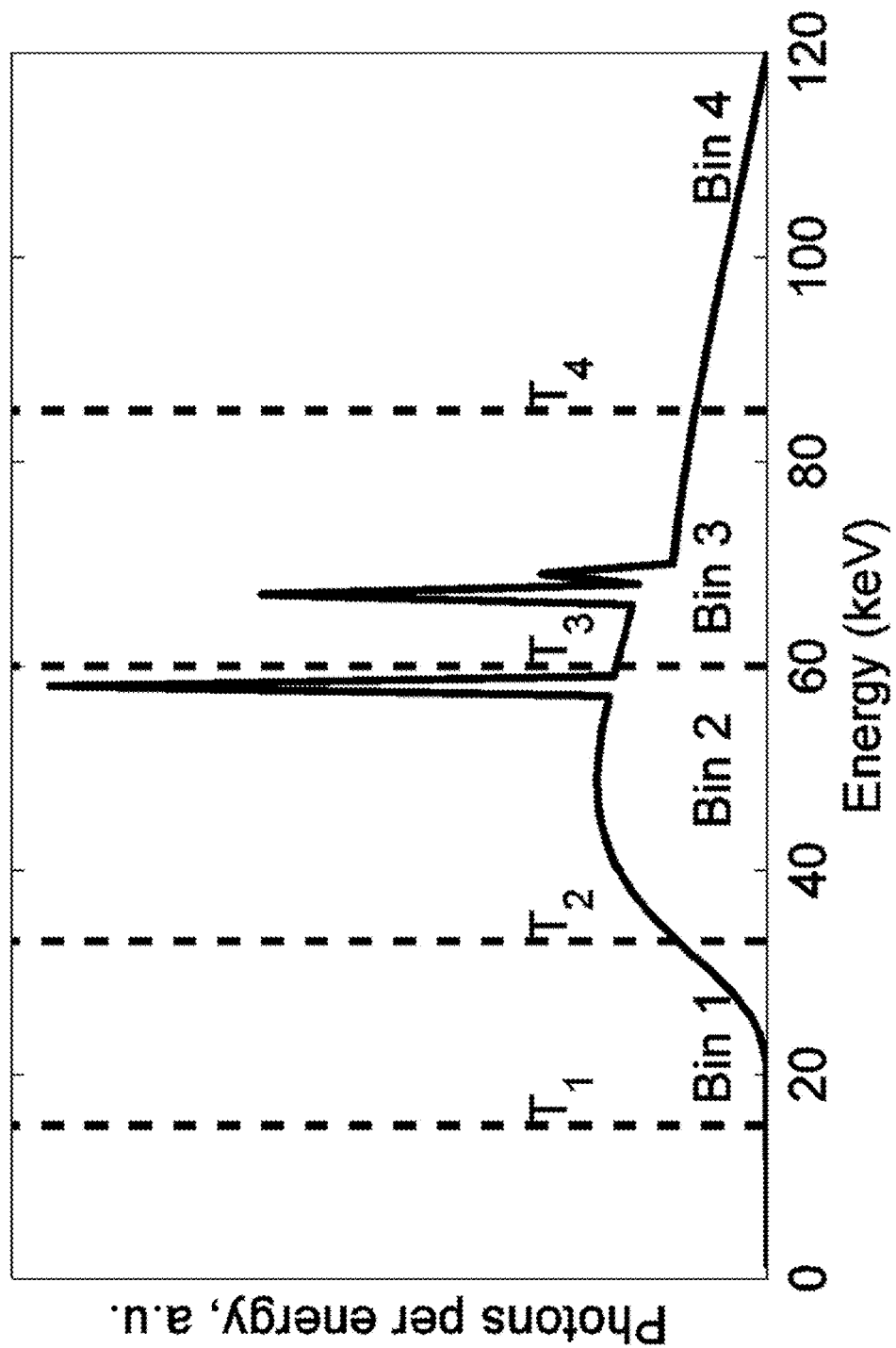
FIG. 4 is a schematic diagram illustrating an example of how a photon counting detector with several energy thresholds divides the spectrum into several energy bins.

In a particular example, the detector is a photon-counting detector as shown in FIG. 3 together with associated analog processing electronics. In this example, the detector 20 includes a reverse-biased photodiode where the photons interact and generate current pulses which are amplified by an amplifier and further processed by a filter to attain a desired pulse shape. Each pulse is then compared to a number N of thresholds $T_1, \ldots, T_N$ using comparators, and a decoder circuit processes the comparator output signals and increments one of several counters, corresponding to the highest threshold which is lower than the pulse height. In this way, the incident x-ray spectrum is divided into a number N of energy bins with one counter each counting the number of registered photons in that bin, as illustrated in FIG. 4. The counter values form the raw data that is read out from the detector and, possibly after further processing in digital processing circuitry, stored by the computer.

Figure 5:
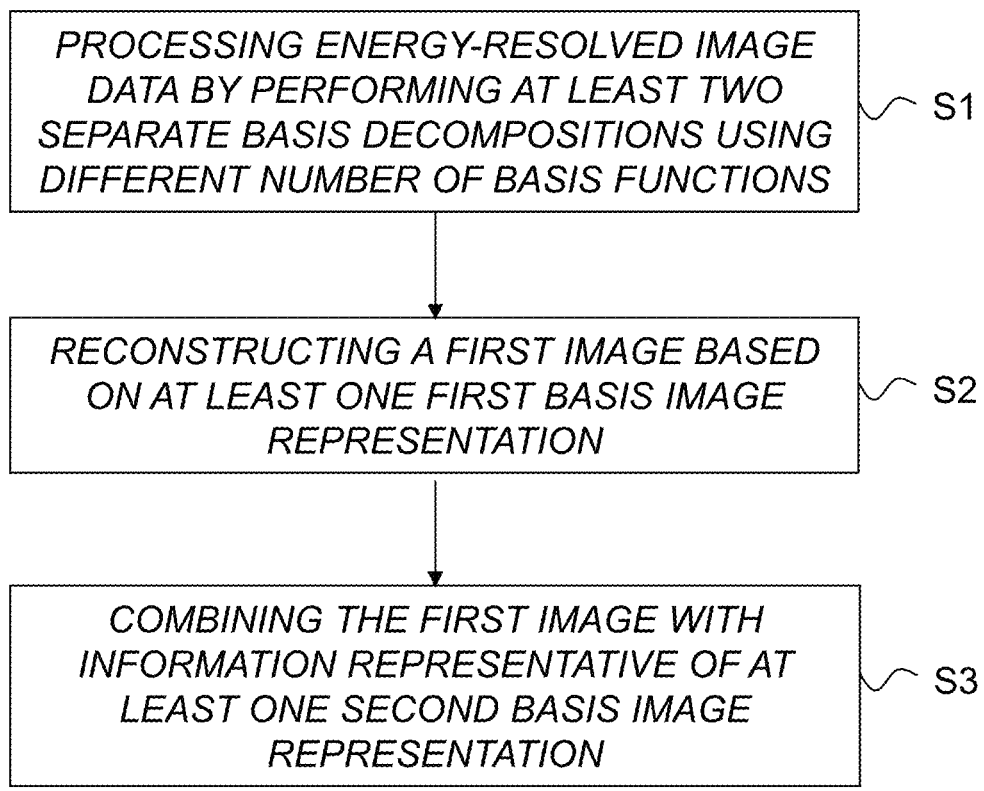
FIG. 5 is a schematic flow diagram illustrating an example of method of image reconstruction according to an embodiment.

FIG. 5 is a schematic flow diagram illustrating an example of method of image reconstruction according to an embodiment. The method basically comprises the following steps:

S1: processing the energy-resolved image data by performing at least two separate basis decompositions using different number of basis functions for modeling linear attenuation, wherein a first basis decomposition is performed using a first smaller set of basis functions to obtain at least one first basis image representation, and wherein a second basis decomposition is performed using a second larger set of basis functions to obtain at least one second basis image representation.

S2: reconstructing a first image based on the at least one first basis image representation obtained from the first basis decomposition.

S3: combining the first image with information representative of the at least one second basis image representation.

By way of example, a second image is reconstructed based on the at least one second basis image representation obtained from the second basis decomposition, and the combining step comprises the step of merging the first image with the second image.

In a particular example, the second image represents a physically interpretable map of the concentration or density of a specific compound or element.

As an example, the information representative of the at least one second basis image representation obtained from the second basis decomposition may be generated in the form of quantitative information representing the concentration or density of a specific compound or element, and the combining step may then comprise the step of displaying the quantitative information in conjunction with the first image.

By way of example, the second larger set of basis functions includes a basis function for modeling the specific compound or element.

For example, the specific element or compound may be iron or a compound including iron.

It should be understood that the first smaller set of basis functions and the second larger set of basis functions may be overlapping or non-overlapping.

In a particular example, the second larger set of basis functions includes the first smaller set of basis functions and an additional basis function.

In an optional embodiment, the first image may be combined with information representative of a set of basis coefficient(s) for the additional basis function.

For example, the additional basis function may reflect the energy dependence of a compound or element without k absorption edges in the diagnostic x-ray energy range.

This may be iron or a or a compound including iron as mentioned above.

By way of example, the first smaller set of basis functions may include at least two basis functions for representing a main part of human body tissue, and the second larger set of basis functions may further include a basis function for representing a compound or element having a linear attenuation falling outside of the span of the at least two basis functions used for representing the main part of human body tissue.

For example, the first smaller set of basis functions may include at least two basis functions for capturing the energy dependence of the photoelectric effect and the Klein-Nishina energy dependent cross section, or for capturing the energy dependence of two distinct materials intended to model human tissue.

It will be understood that each basis decomposition may be based on a model where a combination of at least two basis functions is used to express a representation of at least one linear attenuation coefficient, and each basis decomposition may comprise the step of estimating a set of line integrals of basis coefficients or the corresponding basis coefficients to provide a representation of at least one basis image.

For example, the model may define the number of photons incident per detector element as a function of i) basis coefficients or line integrals of the basis coefficients, and ii) the basis functions.

In a particular example embodiment, two separate basis decompositions are performed on projection image data, resulting in respective line integral estimates of basis function coefficients, where the first decomposition has a smaller set of basis functions in the assumed functional form of the unknown linear attenuation map, and the second decomposition has a larger set of basis functions including a basis function for representing a specific compound or element. A first image reconstruction may then be performed using the line integral estimates from the first decomposition using the smaller number of basis functions, resulting in a display image with relatively low noise level. A second image reconstruction may also be performed using the line integral estimates for the basis coefficient(s) corresponding to the compound or element from the second decomposition using the larger number of basis functions, resulting in a physically interpretable map of the concentration or density of the compound or element. In this example, the display image with relatively low noise level is combined with the physically interpretable map of the concentration or density of the compound or element.

As an example, the display image with relatively low noise level may be combined with the physically interpretable map of the concentration or density of the compound or element by merging the optionally further processed map of the concentration or density of the compound or element with the display image, or otherwise displaying quantitative relevant information relating to the concentration or local density of the compound or element in conjunction with the display image.

For example, the step of displaying quantitative relevant information relating to the concentration or local density of the compound or element may involve displaying an image representing the concentration or local density of the compound or element together with the display image, and/or extracting averages from regions of interest, manually or automatically segmented, in the reconstructed image of the compound or element.

In an optional embodiment, the step of merging the reconstructed images involves color overlay where changes in color intensity is indicative of concentration or local density, or toggling the overlay map (on/off) by inserting to and/or removing the overlay from the display image at a user command.

For example, in a useful application of the proposed technology, the method is based on photon-counting computed tomography.

Figure 6:
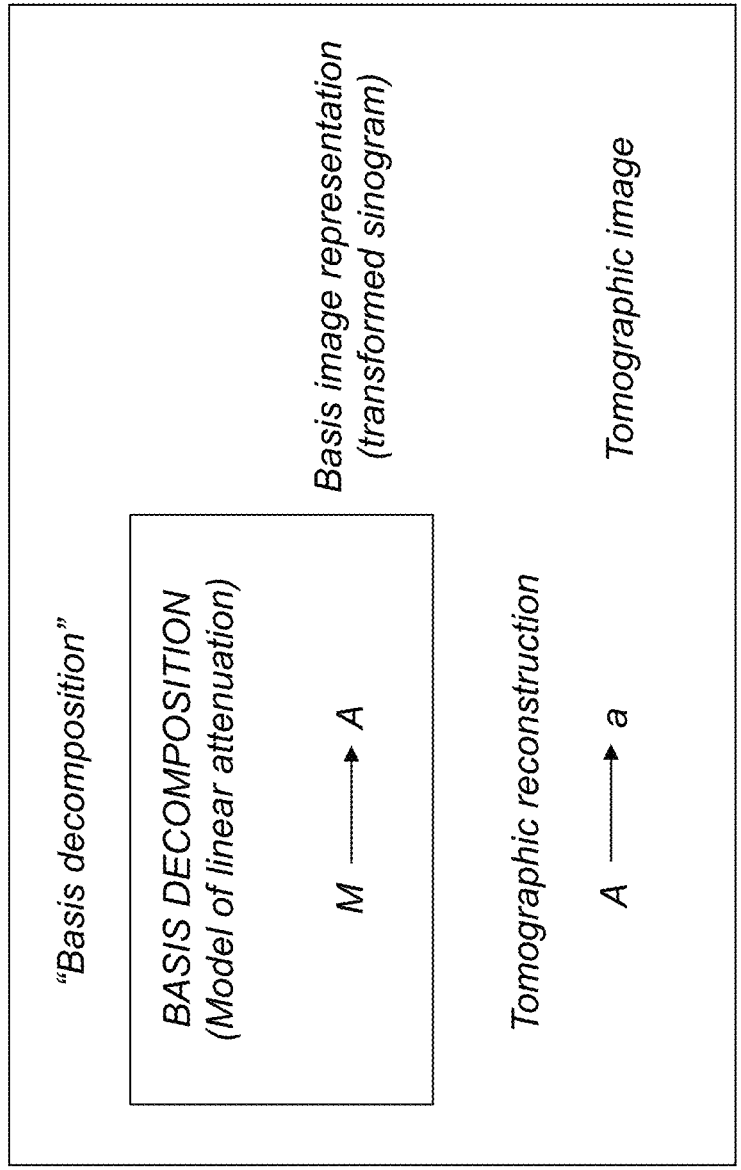
FIG. 6 is a schematic diagram illustrating an example of the basis decomposition procedure(s) and the corresponding resulting basis image representation(s).

FIG. 6 is a schematic diagram illustrating an example of the basis decomposition procedure(s) and the corresponding resulting basis image representation(s). As previously outlined, basis decomposition is normally based on a model of linear attenuation (cofficients), and normally provides a set of line integrals A of basis coefficients based on energy-resolved image data M from the multi-bin detector or an intermediate storage. The output may be seen as basis image representation, or alternatively as a (transformed) sinogram.

From the line integrals A, a tomographic reconstruction to obtain the basis coefficients a may be performed. This procedural step may be regarded as a separate tomographic reconstruction, or may alternatively be seen as part of the overall basis decomposition.

Figure 7:
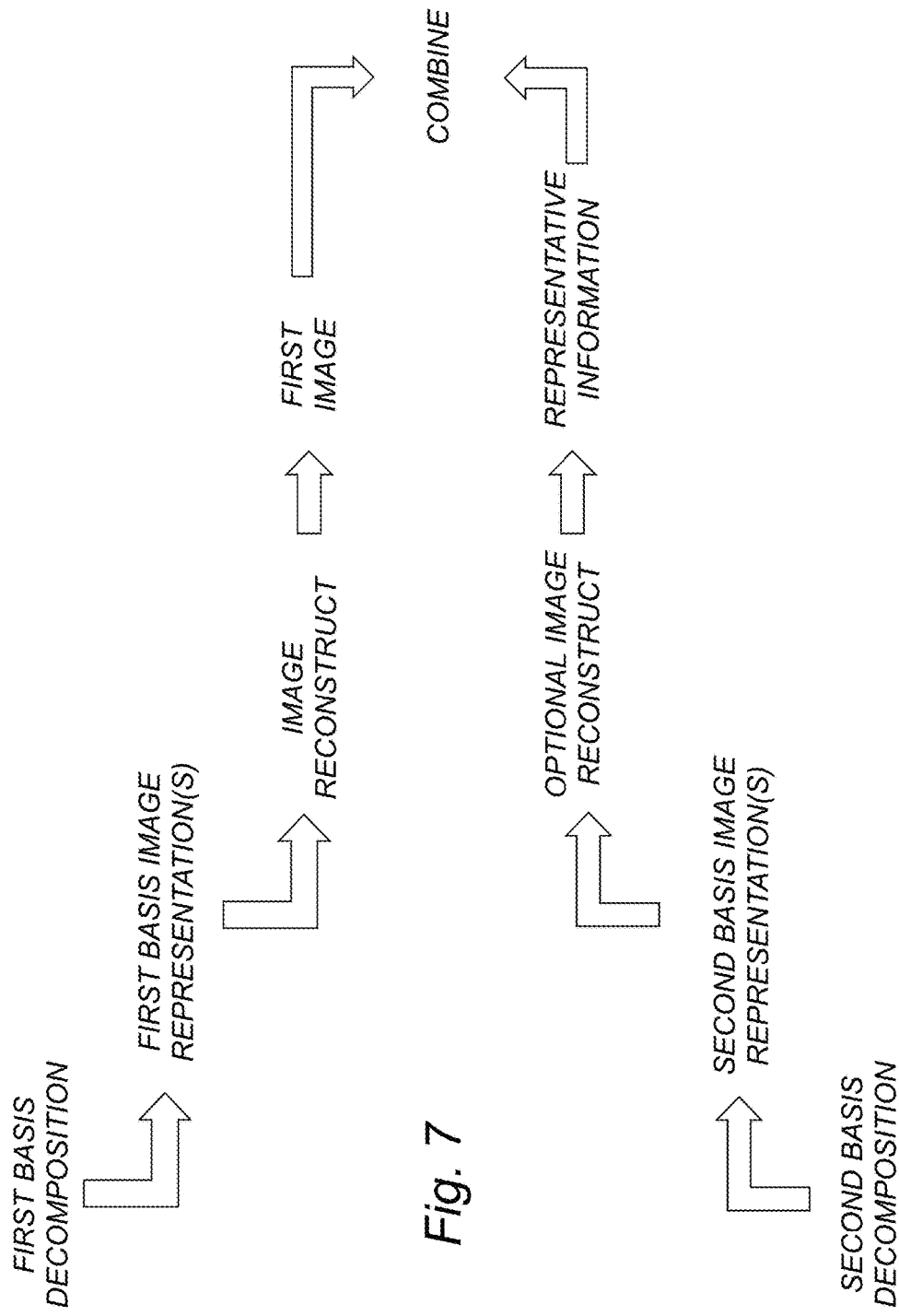
FIG. 7 is a schematic diagram illustrating an example of two parallel processing paths based on separate basis decompositions and the combining of the resulting image information according to an embodiment.
Figure 8:
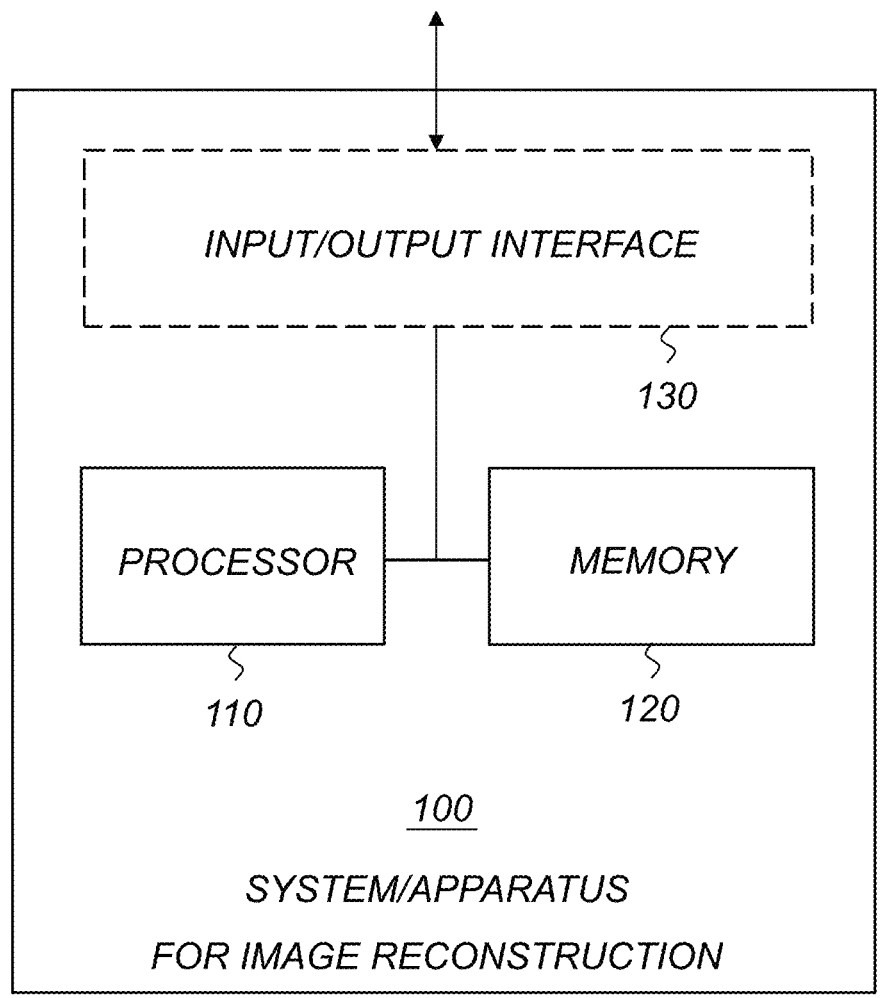
FIG. 8 is a schematic diagram illustrating an example of a system/apparatus for image reconstruction according to an embodiment.
Figure 9:
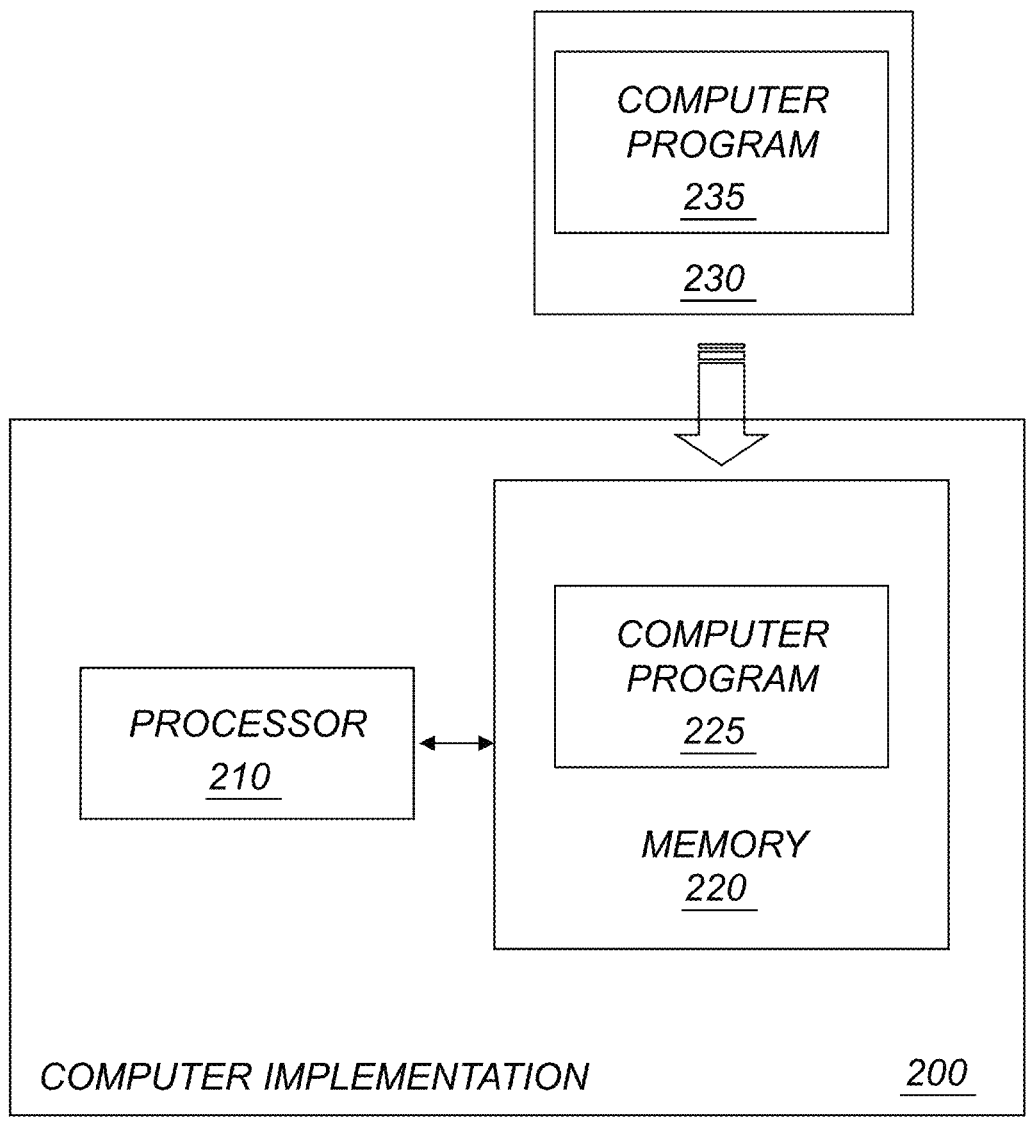
FIG. 9 is a schematic diagram illustrating an example of computer implementation according to an embodiment.

FIG. 7 is a schematic diagram illustrating an example of two parallel processing paths based on separate basis decompositions and the combining of the resulting image information according to an embodiment.

A first basis decomposition is performed using a first smaller set of basis functions to obtain at least one first basis image representation.

A second basis decomposition is performed using a second larger set of basis functions to obtain at least one second basis image representation.

An image reconstruction is performed to provide a first image based on the first basis image representation(s) obtained from the first basis decomposition.

The first image is combined with information representative of the second basis image representation(s) obtained from the second basis decomposition or a corresponding reconstructed image resulting from an optional image reconstruction.

For a better understanding of the proposed technology, various non-limiting example embodiments will now be described in further detail. It may however be useful to begin with a somewhat more detailed overview and analysis of basis decomposition techniques in photon-counting multi-bin systems.

Multi-bin spectrally resolved x-ray detectors utilize direct conversion detection. For each individual photon interaction a voltage pulse is generated, the height of which is close to linear to the energy deposited by the event. Fast readout electronics allow the voltage pulse of each event to be compared to predefined voltage thresholds and increment a counter i if the pulse height was higher than or equal to threshold i ($T_i$) but lower than the threshold i+1 ($T_{i+1}$). With this notation i=1, . . . , N where N is the number of bins and $T_{N+1}$ is set to infinity indicating that all events depositing energies higher than those corresponding to $T_N$ result in an incrementation of the top bin.

In recent years, photon-counting multi-bin spectral computed tomography (multi-bin spectral CT henceforth) has attracted a lot of attention. One of the main reasons is that multi-bin spectral CT allows complete reduction of beam-hardening artefacts and thereby allows for true quantitative CT, where tissue composition in image voxels can be determined with high accuracy and high precision. In short, quantitative CT is achieved by the method of material (or energy) basis decomposition. The method was first introduced in 1976 by Alvarez and Macovski in "Energy-selective reconstruction in x-ray computerized tomography" in Physics of Medicine and Biology, vol 21, pp. 733-44 and is based on the observation that the energy dependence of the linear attenuation coefficient of all bodily constituents to a good approximation can be written as a linear combination of just a few material (or energy) bases:

$$\mu(x, y; E) = \sum_{k=1}^{M} a_k(x, y) f_k(E)$$

where M is normally 2. With multi-bin spectral CT systems it is straightforward to obtain the maximum likelihood estimate of the line integrals of $a_k$, i.e. $\int_l a_k(x,y)ds$ where l is the straight line traversed by the x-ray from the source through the object to a particular detector element in one view (one projection line). From these line integrals the inverse Radon transform is applied to get the set of (maximum likelihood estimates of the) basis coefficients $\{a_k\}$ in each voxel x,y and by insertion in the above equation, the full energy dependence of the linear attenuation coefficient in that voxel has been accurately and precisely estimated. The method was described in detail in 2009 by Roessl and Herrmann in "Cramér-Rao lower bound of basis image noise in multiple-energy X-ray imaging" in Physics in Medicine and Biology, vol. 54, no. 5, pp. 1307-1318.

If iodine is used as a contrast agent during the CT exam, it is normally advisable to increase the set of bases with one by including a base $f_{k+1}(E)$ which is the energy dependency of the linear attenuation coefficient for iodine. The reason is that the sharp increase in x-ray attenuation at the k-edge energy is not captured by the first two bases. By using this extended set of basis functions, the actual iodine content in each voxel can be quantified (in terms of grams per ml or similar physical quantities as opposed to mere gray scale values).

A well-known limitation of the technique is however that as the number of bases M that are estimated from the projection data increases, so does the variance of the estimates. This results in a tradeoff between accuracy (small bias) and precision (small variance in the estimated line integrals $\int_l a_k(x,y)ds$). As M increases, the accuracy improves but the precision deteriorates. This is part of the reason why M=2 is generally applied for human tissues. The other reason why M=2 is generally applied in basis decomposition methods is that it captures the energy dependence of the photon interaction cross sections for the photoelectric effect and incoherent scattering. Theoretical predictions however indicate that other effects such as coherent scattering and molecular binding effects also affect the photon interaction cross section in tissue, and thus that M should be larger than 2 (even in absence of k-edges). These predictions have been verified experimentally on tabulated data, indicating that M might actually be as large as 4; see Bornefalk, "XCOM intrinsic dimensionality for low-Z elements at diagnostic energies", appearing in Medical Physics, vol. 39, no. 2, pp. 654-657, 2012. Thus it is plausible that some bodily constituents are better modeled (in terms of more accurately reconstructed linear attenuation coefficient) with a larger value of M. This could be especially important in the quantification of faint signals (small concentrations) of for instance iron in the liver or past bleedings in the brain as mentioned above.

An investigation by Alvarez "Dimensionality and noise in energy selective x-ray imaging", Medical Physics, vol 40, no. 11, p. 111909-1, 2013 however indicated that the increased accuracy stemming from increasing the value of M is outweighed by the decrease in precision (increase in noise).

From the above is would thus seem proven that it is indeed optimal to perform material basis decomposition (or decomposition using any set of relevant bases such as energy bases or principal component bases) with 2 bases and only using additional bases for each separate k-edge contrast agent that is being used in the examinations, i.e. 3 if only iodine is used, 4 if iodine is used in conjunction with gadolinium and so forth.

The present invention provides a method and system whereby the apparent tradeoff between improved tissue quantification and increased image noise can be overcome. It may be presented in the setting of quantifying small concentrations of iron in the liver or the brain by material basis decomposition using multi-bin computed tomography and is applicable both with and without the presence of iodine contrast agent. A natural extension of the invention may for example be from iron to any element without k-edge in the diagnostic x-ray energy range.

In the following, an example of the proposed technology will be described under the assumption that the abdomen is being imaged by multi-bin CT and that it is desirable to get high quality images. High quality can for example be translated into beam-hardening free and low-noise images. In this non-limiting example it is also assumed that one is interested in determining the iron content in the liver.

In a first step, the projection data is processed in parallel in at least two paths, see figure x. In each path the maximum likelihood estimates of the line integrals $\int_l a_k(x,y)ds$ are determined using model assumptions of different dimensionality, i.e. different values of M in the equation for the linear attenuation coefficient. In a preferred implementation M is 2 and 3 for two different paths if the image acquisition is performed in the absence of iodine. In such a case, the bases in the first path are selected to span soft tissues and bone and could, for example, be the linear attenuation coefficients for soft tissue and fat or those for water and bone. In the second data processing path, an additional base is added, namely the linear attenuation coefficient of iron (or given multiple or fraction thereof).

In the first processing path, the line integrals $\int_l a_k(x,y)ds$ for each projection line l and k=1, 2 are determined using some fitting algorithm to the observed projection data. After tomographic image reconstruction, the basis images $a_k^*(x,y)$, k=1, 2 are obtained. The star (*) indicates that the value is an optimal estimate given the data and some penalty function (least squares or maximum likelihood). From these a beam-hardening free image is reconstructed by, for instance, insertion of the $a_k^*(x,y)$'s in the equation for the linear attenuation coefficient for some choice of the energy E. This results in a syntetic monoenergetic image without beam-hardening.

In the second data processing path, the estimates $a_k^*(x,y)$ for k=1, 2 will be noisier than in the first path since more parameters have been estimated from the data. For that reason $a_k^*(x,y)$ for k=1, 2 are discarded and only $a_3^*(x,y)$ is retained. $a_3^*(x,y)$ is now indicative of the spatial distribution of the iron concentration in the slice.

It can be assumed that $a_3^*(x,y)$ is quite noisy, i.e. has large variance. Generally one wants to quantify the iron over larger regions of interest in the particular organ and for that reason an optional additional data processing step is applied to $a_3^*(x,y)$ to smooth the data. In the simplest form, this can be a low pass filtering but other methods are conceivable such as clustering techniques or even nothing at all. After the additional processing the iron map is denoted $\tilde{a}_3(x,y)$. $\tilde{a}_3(x,y)$ does not have to be visualized by the operator. Instead the image reconstructed from the first path 201 is displayed since it has higher image quality. The information contained in $\tilde{a}_3(x,y)$ can be overlaid the grayscale image from path 201 by, for instance, a color the brightness of which depends on $\tilde{a}_3(x,y)$. For instance, higher concentrations of iron can be displayed as darker shades of pink overlaid over the reconstructed image. For ease of viewing, there can also be a toggle button whereby the iron overlay can be removed or inserted at a simple operator command. Other ways of visualizing the information contained in $\tilde{a}_3(x,y)$ is to let the operator move the mouse pointer over the reconstructed, possibly synthetic mono-energetic image and let the display unit display the concentration $\tilde{a}_3(x,y)$ when the pointer is at position (x,y). While many other possibilities of conveying the information in $\tilde{a}_3(x,y)$ exists, a key element is that while basis material decomposition with an additional basis function tends to increase the noise of the estimators, the raw projection data still contain information that can be extracted and used to generate low noise beam-hardening free images using a reduced number of basis functions.

The following non-limiting example intends to show that obtaining a quantity that is indicative of iron concentration in a slice is easier and requires less assumptions for M=3 than for M=2. Assume first that M=3 and that basis images $a_k^*(x,y)$ for k=1, 2, 3 have been obtained. Let $a^*(x,y)$ denote the corresponding vector in $\mathbb{R}^3$ for a voxel given by x and y. Further let $a_{soft}$, $a_{adipose}$ and $a_{iron}$ be the vectors in $\mathbb{R}_3$ whose elements are the basis coefficients of the linear attenuation coefficients of soft tissue, adipose and iron, respectively. This set of vectors is a basis of $\mathbb{R}^3$, thus $a^*(x,y)$ may be expressed as:

$$a^*(x,y)=\alpha(x,y)a_{soft}+\beta(x,y)a_{adipose}+\gamma(x,y)a_{iron},$$

where $\alpha$, $\beta$ and $\gamma$ are unknown scalar functions. Scalar multiplication of $a^*(x,y)$ for each x and y with a vector $w_{iron}$ in the subspace of $\mathbb{R}^3$ that is orthogonal to $a_{soft}$ and $a_{adipose}$ would thus yield:

$$w_{iron} \cdot a^*(x,y)=\gamma(x,y)(w_{iron} \cdot a_{iron}),$$

from which $\gamma(x,y)$, which is expected to be indicative of the iron concentration in the slice, can be estimated as:

$$\hat{\gamma}(x, y) = \frac{w_{iron} \cdot a^*(x, y)}{w_{iron} \cdot a_{iron}}$$

Assume instead that M=2 and that basis images $a_k^*(x,y)$ for k=1, 2 have been obtained. Like previously, let $a^*(x,y)$ denote the corresponding vector in $\mathbb{R}^2$ for a voxel given by x and y. Further let $a_{soft}$ and $a_{adipose}$ be the vectors in $\mathbb{R}^2$ whose elements are the basis coefficients of the linear attenuation coefficients of soft tissue and adipose. Assume that an actual iron concentration exists in the slice and that its linear attenuation basis coefficients in a voxel given by x and y is:

$$\gamma(x,y)(\gamma_{soft}a_{soft}+\gamma_{adipose}a_{adipose}),$$

where $\gamma$ is an unknown scalar function and $\gamma_{soft}$ and $\gamma_{adipose}$ are known scalars. For simplicity, assume that it is exactly captured in the basis images. Since $a_{soft}$ and $a_{adipose}$ are a basis of $\mathbb{R}^2$, $a^*(x,y)$ may be expressed as:

$$a^*(x,y)=(\alpha(x,y)+\gamma_{soft}\gamma(x,y))a_{soft}+(\beta(x,y)+\gamma_{adipose}\gamma(x,y))a_{adipose},$$

where $\alpha$ and $\beta$ are also unknown scalar functions. This in turn may be rewritten as:

$$a^*(x,y)=(\alpha(x,y)+\gamma_{soft}\gamma(x,y))(a_{soft}-a_{adipose})+(\alpha(x,y)+\gamma_{soft}\gamma(x,y)+\beta(x,y)+\gamma_{adipose}\gamma(x,y))a_{adipose}$$

Scalar multiplication of $a^*(x,y)$ for each x and y with a vector $w_{iron}$ in the subspace of $\mathbb{R}^2$ that is orthogonal to $a_{soft}-a_{adipose}$ thus yields:

$$w_{iron} \cdot a^*(x, y) =$$
$$(\alpha(x, y) + \beta(x, y))(w_{iron} \cdot a_{adipose}) + \gamma(x, y)(\gamma_{soft} + \gamma_{adipose})(w_{iron} \cdot a_{adipose}).$$

Now, in a given region of interest where the type of tissue and its average density is known, $\alpha(x,y)+\beta(x,y)$ may be replaced with a constant $\rho$, assuming that the average density is representative of the sample and that the tissue in question is incompressible. This yields that $\gamma(x,y)$ may be estimated as:

$$\hat{\gamma}(x, y) = \frac{w_{iron} \cdot a^*(x, y) - \rho(w_{iron} \cdot a_{adipose})}{(\gamma_{soft} + \gamma_{adipose})(w_{iron} \cdot a_{adipose})}.$$

If the iron concentration were small, one would expect that the nominator of the right hand side should be a small number resulting from a subtraction, which has limitations in accuracy. Further it is only accurate when the assumption of density and incompressibility are sufficiently accurate.

As mentioned, an example of the application of the proposed technology may involve visualization and/or quantification of a specific element or compound, such as iron or iron-based compounds. For example, liver iron concentration is an important parameter for patients with hemochromatosis (iron overload). Methods of measuring the iron concentration currently include liver biopsy and magnetic resonance imaging. The present invention concerns a method and apparatus whereby the iron concentration in the body can be quantified, e.g. using CT. Another clinically relevant application is in the diagnosis of cerebral hemorrhages. In the examination of suspected hemorrhages, x-ray contrast agent is typically administered before CT image acquisition to detect the bleeding. There is however a risk that residual hemoglobin iron from previous hemorrhages also presents as a highly attenuating background and thus makes the proper diagnosis difficult. It would thus be advantageous with a technology whereby iron concentrations in vivo could be quantified using CT, both with and without iodine or other x-ray contrast agents present, and without reduction of the CT image quality. The proposed invention offers such a technology.

Examples of related solutions in the patent literature include:

U.S. Pat. No. 7,756,239 relates to diagnostic imaging of materials comprising two non K-edge basis materials and a number N of K-edge contrast agents. The imaging procedure is not based on energy-resolved image data from a multi-bin system but rather a method whereby N+2 projections taken with different x-ray spectra (different effective energy) is used to perform material basis decompositions with two bases to capture tissue and N (N greater than or equal to one) K-edge bases.

WO 2007/034359 relates to quantitative material decomposition for spectral computed tomography. Two energy basis functions are used, one for the photoelectric effect and one for the Compton effect. These two bases are used together with an incompressibility assumption to solve for three different basis materials (soft tissue, fat and bone for example). Nota bene that the number of basis functions for non-k-edge materials is however still only two, again illustrating that it is a well-established truth that increasing the value of M in the equation for the linear attenuation coefficient to three for regular tissue increases the noise in the final images, or equivalently as in this case, results in worse quantification precision. The system is not using energy-resolved data from a photon-counting multi-bin detector.

U.S. Pat. No. 7,873,201 relates to reconstruction of x-ray images into basis function components using multiple-energy sources for non-medical inspection systems. A key difference is also that no image processing or bases decomposition with a lower value of the number M of bases is performed in parallel in order to mitigate the deteriorating effect of higher M on image quality.

U.S. Pat. No. 8,855,385 relates to an apparatus and method for multi-energy tissue quantification. A key difference is that this is a dual energy method and only two bases, preferably for water and iodine, are used in the decomposition. A second difference is that the main goal is to quantify fat content, a material that has a linear attenuation coefficient that is within the span of human tissue linear attenuation coefficients as opposed to heavier elements such as iron.

U.S. Pat. No. 8,588,494 relates to a system and method for material decomposition optimization in the image domain. Material basis decomposition is performed with two or more bases using a CT system. A key difference is that photon-counting systems are not applied but rather energy-integrating system. Further, the goal is to improve segmentation in the reconstructed image by incorporation of prior information in terms of the results from neighboring pixels (possibly by means of an iterative approach). This is conceptually similar to using the prior assumption of non-compressibility to allow three material segmentation by dual energy methods. A key difference is therefore that the method does not attempt to quantify materials that have linear attenuation coefficients that fall outside the span of human tissue linear attenuation coefficients.

US Patent Application Publication 2010 0061504 relates only to in-vivo quantification of materials exhibiting k-edge absorption edges.

It will be appreciated that the methods and devices described herein can be combined and re-arranged in a variety of ways.

For example, embodiments may be implemented in hardware, or in software for execution by suitable processing circuitry, or a combination thereof.

The steps, functions, procedures, modules and/or blocks described herein may be implemented in hardware using any conventional technology, such as discrete circuit or integrated circuit technology, including both general-purpose electronic circuitry and application-specific circuitry.

Particular examples include one or more suitably configured digital signal processors and other known electronic circuits, e.g. discrete logic gates interconnected to perform a specialized function, or Application Specific Integrated Circuits (ASICs).

Alternatively, at least some of the steps, functions, procedures, modules and/or blocks described herein may be implemented in software such as a computer program for execution by suitable processing circuitry such as one or more processors or processing units.

Examples of processing circuitry includes, but is not limited to, one or more microprocessors, one or more Digital Signal Processors (DSPs), one or more Central Processing Units (CPUs), video acceleration hardware, and/or any suitable programmable logic circuitry such as one or more Field Programmable Gate Arrays (FPGAs), or one or more Programmable Logic Controllers (PLCs).

It should also be understood that it may be possible to re-use the general processing capabilities of any conventional device or unit in which the proposed technology is implemented. It may also be possible to re-use existing software, e.g. by reprogramming of the existing software or by adding new software components.

The proposed technology thus provides an image reconstruction system configured to perform the method described herein.

In particular, there is provided a system for image reconstruction based on energy-resolved image data from a photon-counting multi-bin detector or an intermediate storage. The system is configured to process the energy-resolved image data by performing at least two separate basis decompositions using different number of basis functions for modeling linear attenuation. The system is configured to perform a first basis decomposition using a first smaller set of basis functions to obtain at least one first basis image representation. The system is also configured to perform a second basis decomposition using a second larger set of basis functions to obtain at least one second basis image representation. The system is further configured to reconstruct a first image based on said at least one first basis image representation obtained from the first basis decomposition. The system is also configured to combine the first image with information representative of said at least one second basis image representation.

By way of example, the system is configured to reconstruct a second image based on the at least one second basis image representation obtained from the second basis decomposition, and wherein the system is configured to merge the first image with the second image.

For example, the system may be configured to reconstruct the second image in the form of a physically interpretable map of the concentration or density of a specific compound or element.

In a particular example, the system is configured to generate the information representative of the at least one second basis image representation in the form of quantitative information representing the concentration or density of a specific compound or element, and wherein the system is configured to display the quantitative information in conjunction with the first image.

As an example, the system may be configured to perform the second basis decomposition using a second larger set of basis functions that includes a basis function for modeling the specific compound or element.

In particular, the system may be configured to perform the second basis decomposition using a second larger set of basis functions that includes a basis function for modeling iron or a compound including iron.

In a non-limiting example, the system is configured to perform the second basis decomposition using a second larger set of basis functions that includes the first smaller set of basis functions and an additional basis function, and wherein the system is configured to combine the first image with information representative of a set of basis coefficient(s) for the additional basis function.

By way of example, the system may be configured to perform the first basis decomposition using a first smaller set of basis functions that includes at least two basis functions for representing a main part of human body tissue, and wherein the system is configured to perform the second basis decomposition using a second larger set of basis functions that further includes a basis function for representing a compound or element having a linear attenuation falling outside of the span of the at least two basis functions used for representing the main part of human body tissue.

In a particular example, the system is configured to perform two separate basis decompositions on projection image data, resulting in respective line integral estimates of basis function coefficients, where the first decomposition has a smaller set of basis functions in the assumed functional form of the unknown linear attenuation map, and the second decomposition has a larger set of basis functions including a basis function for representing a specific compound or element. The system may be configured to perform a first image reconstruction using the line integral estimates from the first decomposition using the smaller number of basis functions, resulting in a display image with relatively low noise level. The system may also be configured to perform a second image reconstruction using the line integral estimates for the basis coefficient(s) corresponding to the compound or element from the second decomposition using the larger number of basis functions, resulting in a physically interpretable map of the concentration or density of the compound or element. The system may further be configured to combine the display image with relatively low noise level with the physically interpretable map of the concentration or density of the compound or element.

For example, the system may be configured to combine the display image with relatively low noise level with the physically interpretable map of the concentration or density of said compound or element by merging the optionally further processed map of the concentration or density of the compound or element with the display image, or otherwise displaying quantitative relevant information relating to the concentration or local density of the compound or element in conjunction with the display image.

Optionally, the system is configured display an image representing the concentration or local density of the compound or element together with the display image, and/or extract averages from regions of interest, manually or automatically segmented, in the reconstructed image of the compound or element.

There is also provided an imaging system comprising such a system for image reconstruction.

In a particular example, the system/apparatus 100 for image reconstruction comprises a processor 110 and a memory 120, the memory comprising instructions executable by the processor, whereby the processor is operative to perform the basis decompositions, image reconstruction(s) and combining of information, as illustrated in FIG. 11. Optionally, the system comprises an input/output interface 130 for receiving input data and outputting resulting output data.

In this particular example, at least some of the steps, functions, procedures, modules and/or blocks described herein are implemented in a computer program, which is loaded into the memory for execution by processing circuitry including one or more processors. The processor(s) and memory are interconnected to each other to enable normal software execution. An optional input/output device may also be interconnected to the processor(s) and/or the memory to enable input and/or output of relevant data such as input parameter(s) and/or resulting output parameter(s).

The term 'processor' should be interpreted in a general sense as any system or device capable of executing program code or computer program instructions to perform a particular processing, determining or computing task.

The processing circuitry including one or more processors is thus configured to perform, when executing the computer program, well-defined processing tasks such as those described herein.

The processing circuitry does not have to be dedicated to only execute the above-described steps, functions, procedure and/or blocks, but may also execute other tasks. FIG. 12 is a schematic diagram illustrating another example of computer implementation according to an embodiment.

In a particular embodiment, there is provided a computer program 225; 235 for use with a photon-counting multi-bin x-ray detector. The computer program 225; 235 comprises instructions, which when executed by at least one processor 110; 210, cause the at least one processor to:

process energy-resolved image data from a photon-counting multi-bin detector or an intermediate storage by performing at least two separate basis decompositions using different number of basis functions for modeling linear attenuation, wherein a first basis decomposition is performed using a first smaller set of basis functions to obtain at least one first basis image representation, and wherein a second basis decomposition is performed using a second larger set of basis functions to obtain at least one second basis image representation; and perform image reconstruction based on the at least one first basis image representation obtained from the first basis decomposition and the at least one second basis image representation obtained from the second basis decomposition.

The proposed technology also provides a computer-program product comprising a computer-readable medium 220; 230 having stored thereon such a computer program.

By way of example, the software or computer program 225; 235 may be realized as a computer program product, which is normally carried or stored on a computer-readable medium 220; 230, in particular a non-volatile medium. The computer-readable medium may include one or more removable or non-removable memory devices including, but not limited to a Read-Only Memory (ROM), a Random Access Memory (RAM), a Compact Disc (CD), a Digital Versatile Disc (DVD), a Blu-ray disc, a Universal Serial Bus (USB) memory, a Hard Disk Drive (HDD) storage device, a flash memory, a magnetic tape, or any other conventional memory device. The computer program may thus be loaded into the operating memory of a computer or equivalent processing device for execution by the processing circuitry thereof.

The flow diagram or diagrams presented herein may be regarded as a computer flow diagram or diagrams, when performed by one or more processors. A corresponding device, system and/or apparatus may be defined as a group of function modules, where each step performed by the processor corresponds to a function module. In this case, the function modules are implemented as a computer program running on the processor. Hence, the device, system and/or apparatus may alternatively be defined as a group of function modules, where the function modules are implemented as a computer program running on at least one processor.

The computer program residing in memory may thus be organized as appropriate function modules configured to perform, when executed by the processor, at least part of the steps and/or tasks described herein.

Alternatively it is possibly to realize the modules predominantly by hardware modules, or alternatively by hardware. The extent of software versus hardware is purely implementation selection.

The proposed technology also provides an arrangement for visualization and/or quantification of an in vivo compound or element not exhibiting k absorption edges. The arrangement comprises a photon-counting multi-bin detector mountable in a computed tomography gantry. The arrangement also comprises a processing device capable of decomposing multi-bin projection measurements in at least two parallel processing paths using different number of basis functions for reconstructing corresponding images. The arrangement further comprises a graphic device capable of merging images resulting from the parallel processing paths including at least one reconstructed display image and a reconstructed image, for example an overlay map, of the compound or element.

By way of example, the processing device is capable of performing a first basis decomposition in a first processing path to provide at least one first basis image representation for reconstructing the display image(s), and a second basis decomposition in a second processing path to provide at least one second basis image representation for reconstructing the overlay map of the compound or element.

In a particular example, the arrangement further comprises a device capable of extracting and displaying quantitative data regarding local density or concentration of the element or compound in a region of interest defined in the overlay map or in the display image.

The embodiments described above are merely given as examples, and it should be understood that the proposed technology is not limited thereto. It will be understood by those skilled in the art that various modifications, combinations and changes may be made to the embodiments without departing from the present scope as defined by the appended claims. In particular, different part solutions in the different embodiments can be combined in other configurations, where technically possible.

The invention claimed is:

1. A method of image reconstruction based on energy-resolved image data from a photon-counting multi-bin detector or an intermediate storage, wherein said method comprises:
   processing the energy-resolved image data by performing at least two separate basis decompositions using different number of basis functions for modeling linear attenuation,
   wherein a first basis decomposition is performed using a first smaller set of basis functions to obtain at least one first basis image representation, and
   wherein a second basis decomposition is performed using a second larger set of basis functions to obtain at least one second basis image representation; and
   reconstructing a first image based on said at least one first basis image representation obtained from the first basis decomposition; and
   combining the first image with information representative of said at least one second basis image representation,
   wherein two separate basis decompositions are performed on projection image data, resulting in respective line integral estimates of basis function coefficients, where the first decomposition has a smaller set of basis functions in the assumed functional form of the unknown linear attenuation map, and the second decomposition has a larger set of basis functions including a basis function for representing a specific compound or element,
   wherein a first image reconstruction is performed using the line integral estimates from the first decomposition using the smaller number of basis functions, resulting in a display image with relatively low noise level,
   wherein a second image reconstruction is performed using the line integral estimates for the basis coefficient(s) corresponding to said compound or element from the second decomposition using the larger number of basis functions, resulting in a physically interpretable map of the concentration or density of said compound or element, and
   wherein the display image with relatively low noise level is combined with the physically interpretable map of the concentration or density of said compound or element.

2. The method of claim 1, wherein the display image with relatively low noise level is combined with the physically interpretable map of the concentration or density of said compound or element by merging the optionally further processed map of the concentration or density of said compound or element with the display image or otherwise displaying quantitative relevant information relating to the concentration or local density of said compound or element in conjunction with the display image.

3. The method of claim 1, wherein the step of merging the reconstructed images involves color overlay where changes in color intensity is indicative of concentration or local density, or toggling the overlay map by inserting to and/or removing the overlay from the display image at a user command.

4. A system for image reconstruction based on energy-resolved image data from a photon-counting multi-bin detector or an intermediate storage,
   wherein the system is configured to process the energy-resolved image data by performing at least two separate basis decompositions using different number of basis functions for modeling linear attenuation,
   wherein the system is configured to perform a first basis decomposition using a first smaller set of basis functions to obtain at least one first basis image representation,
   wherein the system is configured to perform a second basis decomposition using a second larger set of basis functions to obtain at least one second basis image representation; and
   wherein the system is configured to reconstruct a first image based on said at least one first basis image representation obtained from the first basis decomposition;
   wherein the system is configured to combine the first image with information representative of said at least one second basis image representation,
   wherein the system is configured to perform two separate basis decompositions on projection image data, resulting in respective line integral estimates of basis function coefficients, where the first decomposition has a smaller set of basis functions in the assumed functional form of the unknown linear attenuation map, and the second decomposition has a larger set of basis functions including a basis function for representing a specific compound or element,
   wherein the system is configured to perform a first image reconstruction using the line integral estimates from the first decomposition using the smaller number of basis functions, resulting in a display image with relatively low noise level,
   wherein the system is configured to perform a second image reconstruction using the line integral estimates for the basis coefficient(s) corresponding to said compound or element from the second decomposition using the larger number of basis functions, resulting in a physically interpretable map of the concentration or density of said compound or element, and
   wherein the system is configured to combine the display image with relatively low noise level with the physically interpretable map of the concentration or density of said compound or element.

\* \* \* \* \*